(12) United States Patent
Domloge et al.

(10) Patent No.: US 11,628,133 B2
(45) Date of Patent: Apr. 18, 2023

(54) USES OF THE PEPTIDE OF SEQUENCE HIS-D-TRP-ALA-TRP-D-PHE-LYS-NH2 FOR REDUCING OR DELAYING THE APPEARANCE OF CELL SENESCENCE AND SIGNS OF SKIN AGING

(71) Applicant: ISP INVESTMENTS LLC, Wilmington, DE (US)

(72) Inventors: Nouha Domloge, Opio (FR); Catherine Gondran, Seillans (FR); Ludivine Mur, Biot (FR)

(73) Assignee: ISP Investments LLC, Wilmington, DE (US)

( * ) Notice: Subject to any disclaimer, the term of this patent is extended or adjusted under 35 U.S.C. 154(b) by 375 days.

(21) Appl. No.: 15/565,226

(22) PCT Filed: Apr. 8, 2016

(86) PCT No.: PCT/EP2016/057813
§ 371 (c)(1),
(2) Date: Oct. 9, 2017

(87) PCT Pub. No.: WO2016/162512
PCT Pub. Date: Oct. 13, 2016

(65) Prior Publication Data
US 2018/0078483 A1 Mar. 22, 2018

(30) Foreign Application Priority Data
Apr. 10, 2015 (FR) .................................. 1553139

(51) Int. Cl.
*A61K 8/64* (2006.01)
*A61Q 19/02* (2006.01)
*A61Q 19/08* (2006.01)

(52) U.S. Cl.
CPC .............. *A61K 8/64* (2013.01); *A61Q 19/02* (2013.01); *A61Q 19/08* (2013.01); *A61K 2800/78* (2013.01)

(58) Field of Classification Search
None
See application file for complete search history.

(56) References Cited

U.S. PATENT DOCUMENTS

| 2009/0181888 A1 | 7/2009 | Murakami et al. |
| 2015/0057230 A1* | 2/2015 | Park ..................... A61K 8/64 514/17.2 |

FOREIGN PATENT DOCUMENTS

| EP | 1994939 A1 | 11/2008 |
| EP | 2666780 A1 | 11/2013 |

OTHER PUBLICATIONS

Macrae, Fiona and Kisiel, Ryan, "Anti-wrinkle creams that really work . . . but only with a magic ingredient." Daily Mail, last edited Mar. 7, 2013.*
Böhm, Markus et al, "Collagen metabolism is a novel target of the nueropeptide alpha-melanocyte stimulating hormone." J. Biol. Chem. (2004) 279(8) p. 6959-6966.*
The press release from Massage Magazine of Jul. 22, 2011.*
Le Tourneau, Christophe et al, "Dose escalation methods in phase I cancer clinical trials." J. Natl. Cancer Inst. (2009) 101 p. 708-720.*
Sales literature for Biotide from Incospharm, published 2017.*
Choi, Won Seon, "Involvment of tgf-beta in skin photoaging." PhD thesis (2005) Massachusetts Institute of Technology, department of Biomedical Engineering.*
Oida, Takatoku and Weiner, Howard L.; "Depletion of tgf-beta from fetal bovine serum." J. Immunol. Method. (2010) 362 p. 195-198.*
Progeria fibroblast cell culture procedures, https://www.progeriaresearch.org/fibroblast-cell-culture-protocols/, downloaded May 6, 2019.*
Bhadra, Rajarshi et al, "Intrinsic tfg-beta signalling promotes age-dependent cd8+ t cell polyfunctionality attrition," J. Clin. Invest. (2014) 124(6) p. 2441-2455.*
Lush UK's description of glycerin, https://uk.lush.com/ingredients/glycerine, downloaded Jan. 30, 2019.*
Gorouhi, F. and Maibach, H. I., "Role of topical peptides in preventing or treating aged skin." J. Cosmetic Sci. (2009) 31 p. 327-345.*
Jayawikreme, Channa K. et al, "Discovery and structure-function analysis of alpha-melanocyte-stimulating hormone antagonists." J. Biol. Chem. (1994) 269(47) p. 29846-29854.*
Mentel, M. et al; "Innovative peptide technologies foreven, young, and healthy looking skin." SOFW-Journal (2012) 138 p. 22-31.*
Varga, John et al, "Transforming growth factor beta (tgf-beta) causes a persistent increase in steady-state maounts of type 1 and type 111 collagen and fibronectin mmas in normal human dermal fibroblasts." Biochem. J. (1987) 247) 597-604.*
PCT, International Search Report (with English translation), International Application No. PCT/EP2016/057813, 8 pages, Jun. 27, 2016.
"Rapid Age Spot and Pigment Lightening Serum" product information by Mintel, XP002750761,5 pages, Jan. 2012.
Barbul, A., Proline Precursors to Sustain Mammalian Collagen Synthesis, *The Journal of Nutrition, 7th Amino Acid Assessment Workshop*, pp. 2021S-2024S (2008).

(Continued)

*Primary Examiner* — Fred H Reynolds
(74) *Attorney, Agent, or Firm* — Thompson Hine LLP

(57) ABSTRACT

The present invention relates to the cosmetic use of a composition including, as the active agent, 0.1 to 1 µM of a synthetic peptide of sequence His-D-Trp-Ala-Trp-D-Phe-Lys-NH2 or one of the salts thereof in a physiologically suitable medium, in order to reduce or delay the appearance of cell senescence and signs of skin aging. The present invention also relates to a method for cosmetic treatment which relates to these novel uses, including comprising the steps of applying the composition, topically, at least once per day, for a period of at least two days.

9 Claims, 5 Drawing Sheets
Specification includes a Sequence Listing.

(56) References Cited

OTHER PUBLICATIONS

Mancini, M. et al., "MIcroRNAs in human skin ageing," *Ageing Research Reviews* 17, pp. 9-15 (2014).
Pałka, J.A. et al., "Modulation of Prolidase Activity during in Vitro Aging of Human Skin Fibroblasts the Role of Extracellular Matrix Collagen," *Tokai J. Exp. Clin. Med.* 21(4-6), pp. 207-213 (1996).
Sawyer, T.K. et al., "Discovery and Structure-Activity Relationships of novel α-Melanocyte-Stimulating Hormone Inhibitors," *Peptide Research* 2(1), pp. 140-146 (1989).
Son, E.D. et al., "Alpha-Ketoglutarate Stimulates Procollagen Production in Cultured Human Dermal Fibroblasts, and Decreases UVB-Induced Wrinkle Formation Following Topical Application on the Dorsal Skin of Hairless Mice," *Biol. Pharm. Bull.* 30(8), pp. 1395-1399 (2007).
Surazynski, A. et al., "Prolidase-dependent regulation of collagen biosynthesis," *Amino Acids* 35, pp. 731-738 (2008).

\* cited by examiner

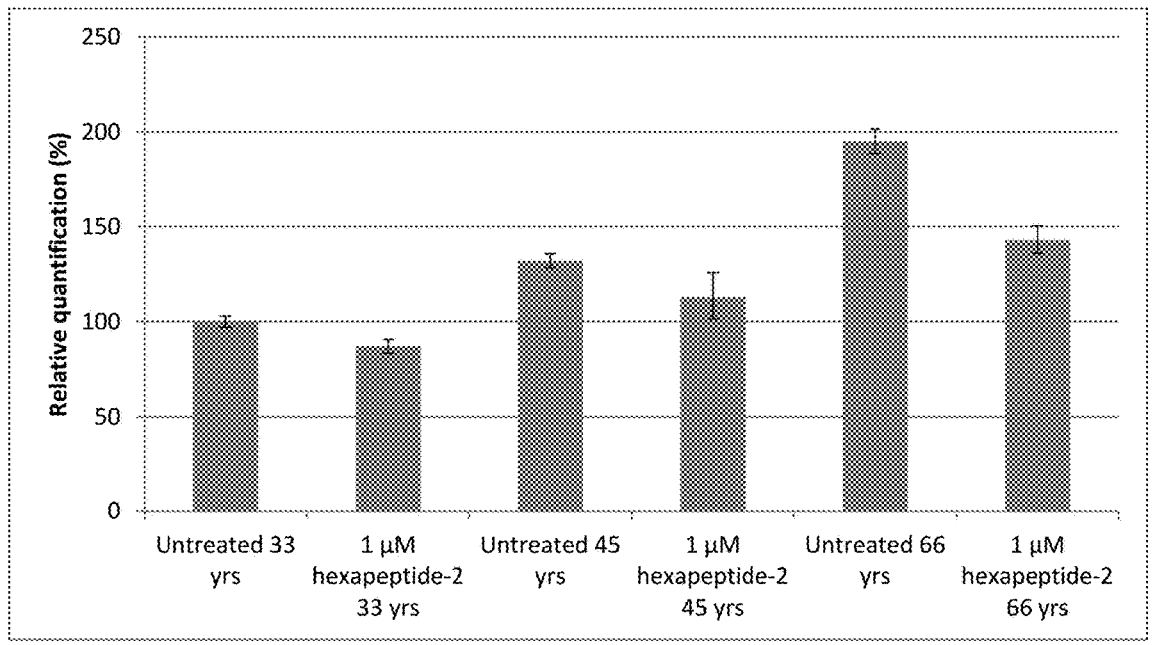
Figure 1: Study of the expression of miRNA-29a 3p in human fibroblasts from donors of different ages
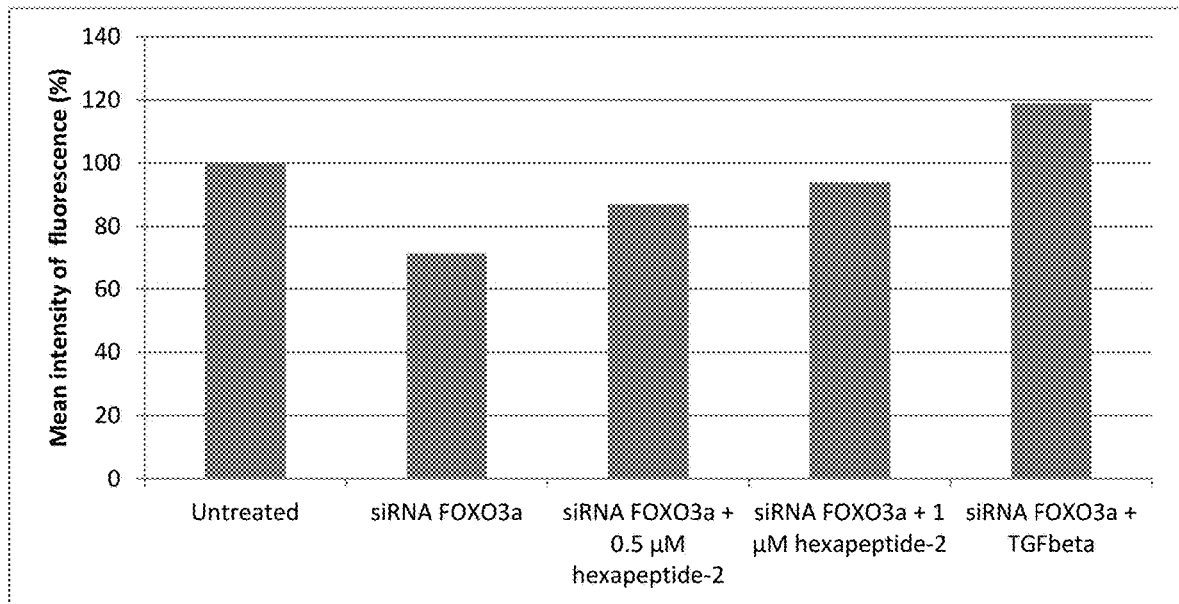
Figure 2: Evaluation of the effect of hexapeptide-2 on the expression of collagen I in human fibroblasts rendered senescent by transfection with the siRNA FOXO3a

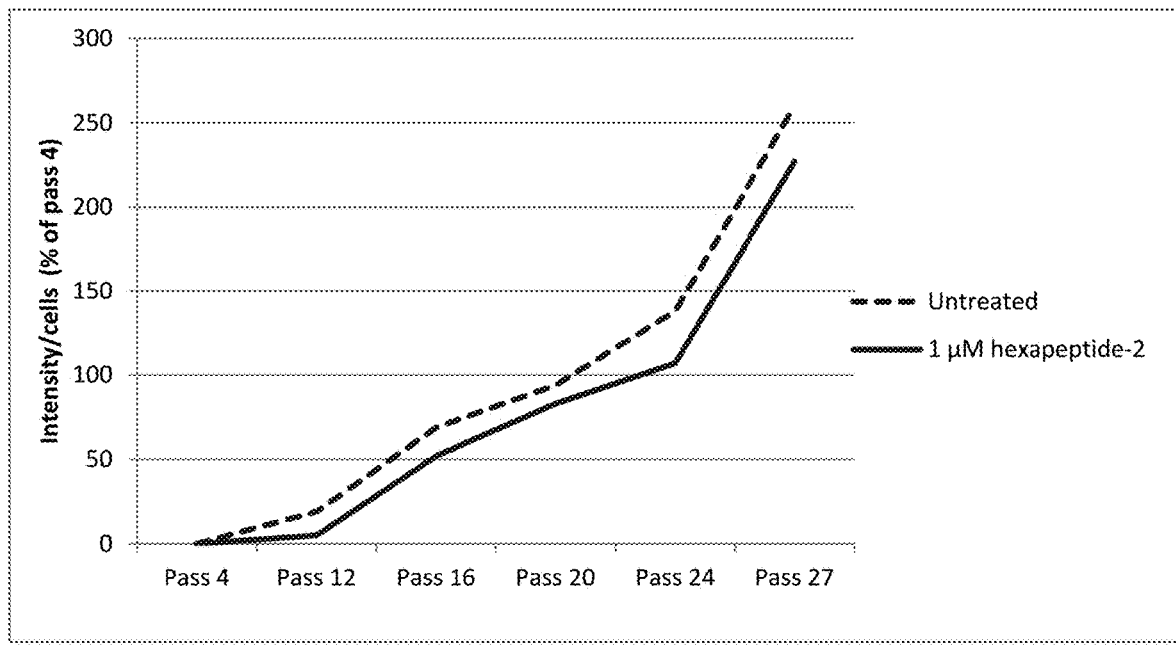

Figure 3: Evaluation of the effect of hexapeptide-2 on the activity of β-galactosidase in human fibroblasts rendered senescent by replicative senescence (long-term treatment)

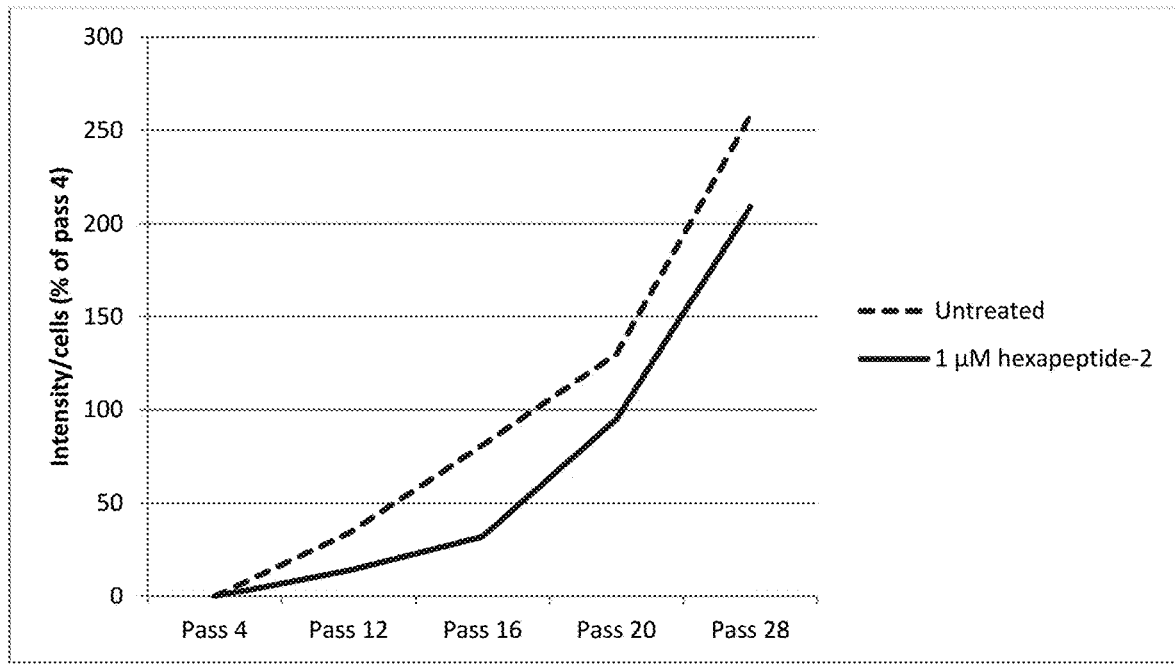

Figure 4: Evaluation of the effect of hexapeptide-2 on the activity of β-galactosidase in human fibroblasts which are senescent by replicative senescence, in the presence of hexapeptide-2 (short-term treatment)

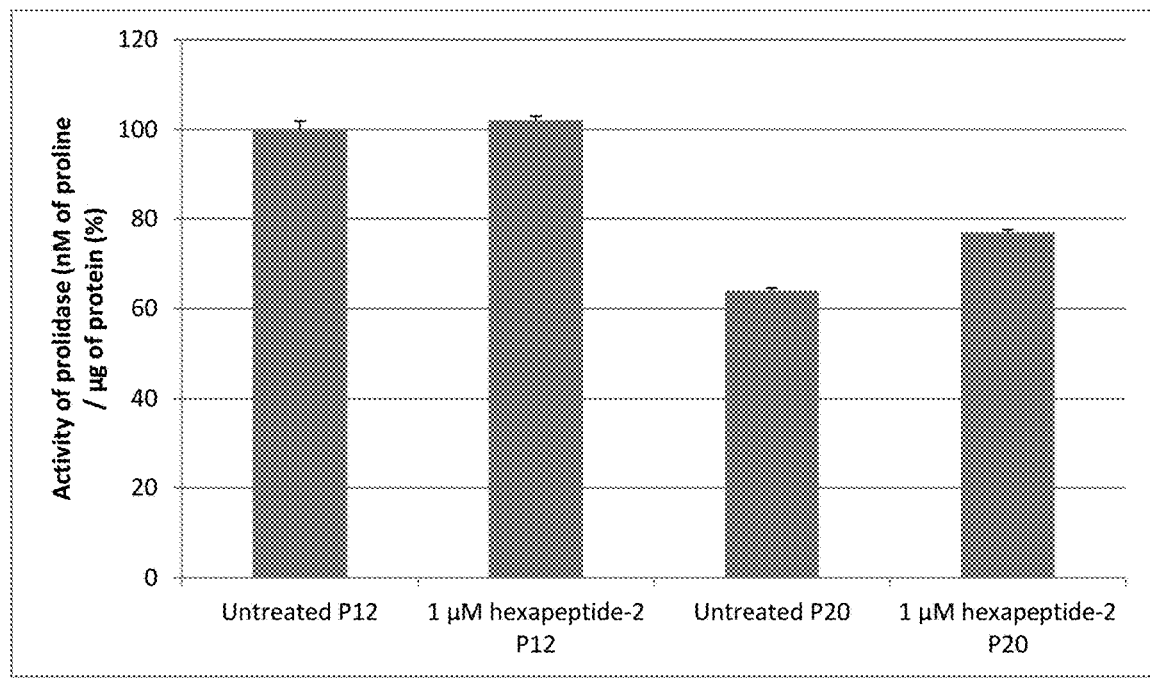
Figure 5: Evaluation of the effect of hexapeptide-2 on the activity of prolidase in human fibroblasts rendered senescent by replicative senescence (long-term treatment)
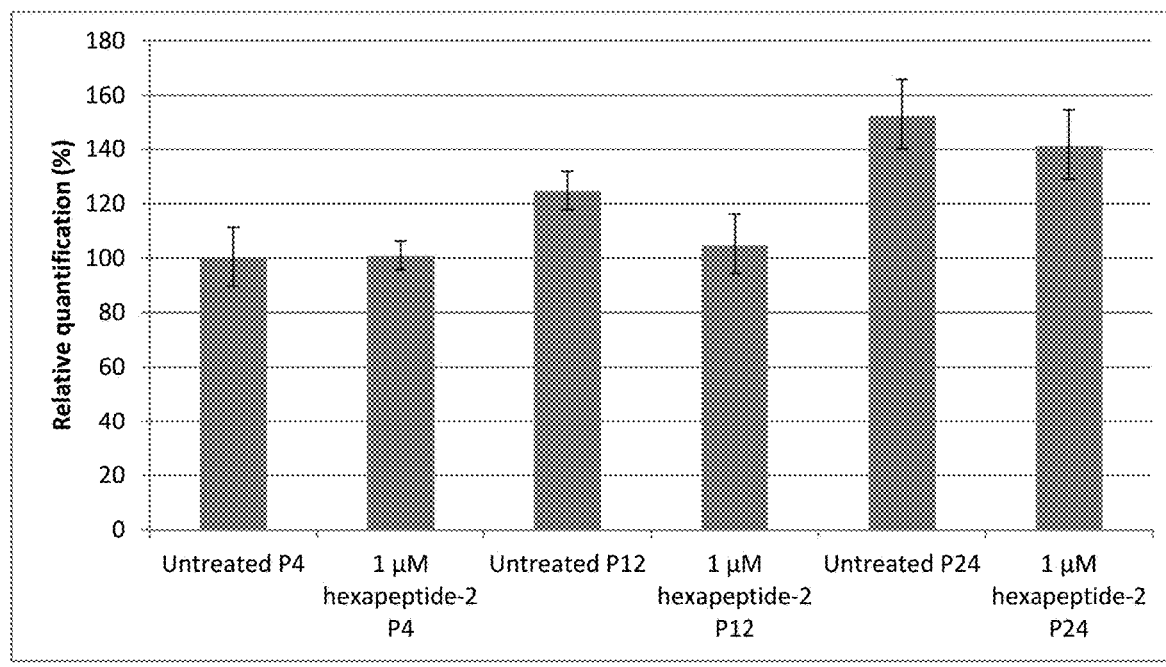
Figure 6: Evaluation of the effect of hexapeptide-2 on the expression of miRNA-29a 3p in human fibroblasts rendered senescent by replicative senescence (long-term treatment)

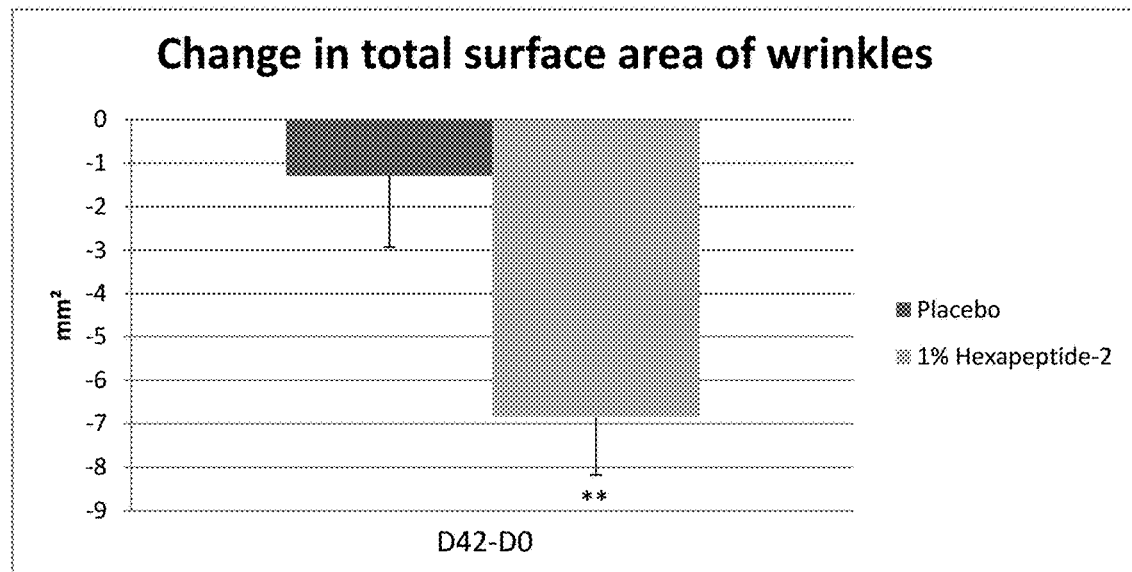
Figure 7: Effect of 1% hexapeptide-2 on the total surface area of wrinkles, evaluated by clinical study
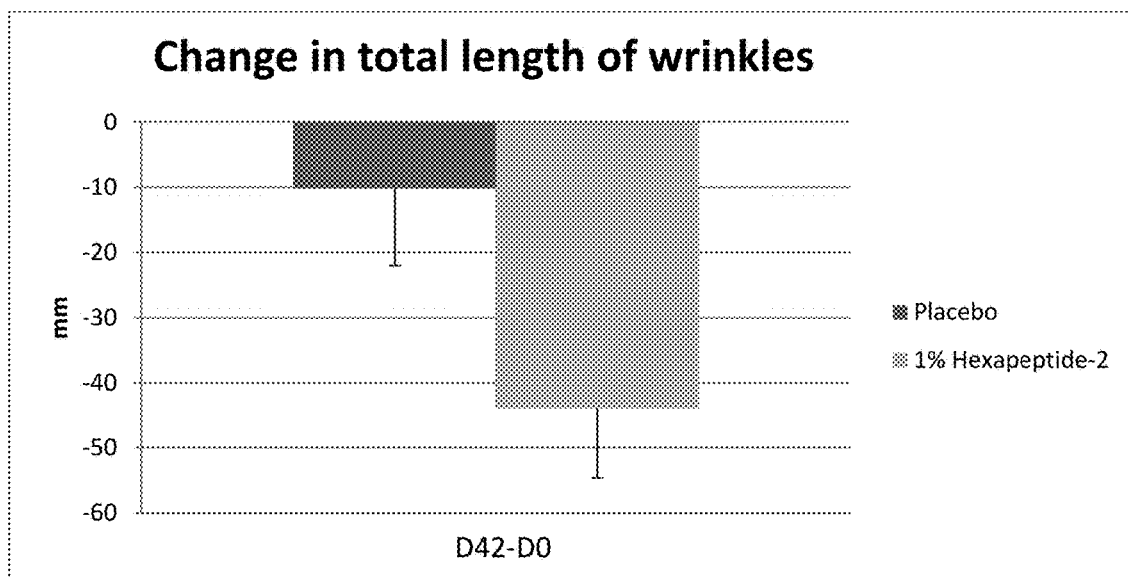
Figure 8: Effect of 1% hexapeptide-2 on the total length of wrinkles, evaluated by clinical study

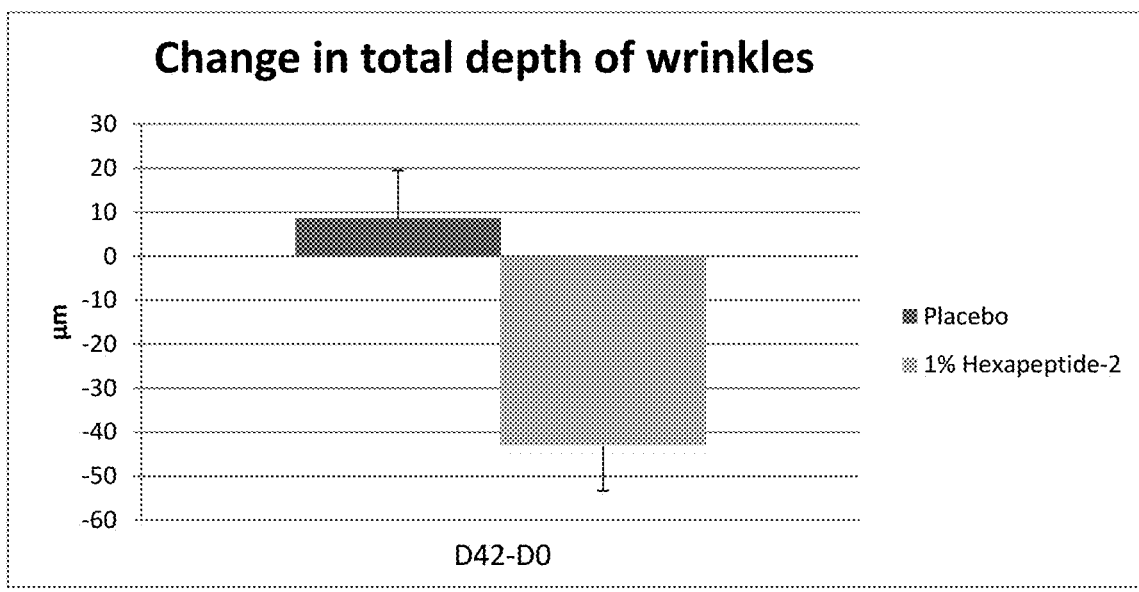
Figure 9: Effect of 1% hexapeptide-2 on the total depth of wrinkles, evaluated by clinical study

USES OF THE PEPTIDE OF SEQUENCE HIS-D-TRP-ALA-TRP-D-PHE-LYS-NH2 FOR REDUCING OR DELAYING THE APPEARANCE OF CELL SENESCENCE AND SIGNS OF SKIN AGING

CROSS-REFERENCE TO RELATED APPLICATIONS

This application is a National Stage filing of International Application No. PCT/EP2016/057813, filed Apr. 8, 2016, which claims priority of French Patent Application No. 1553139 filed Apr. 10, 2015, which are incorporated herein by reference in their entireties.

The present invention relates to the field of cosmetic and dermato-pharmaceutical active agents as well as to cosmetic treatment methods pertaining thereto.

The present invention pertains to the novel cosmetic use of a composition comprising a synthetic peptide with the sequence His-D-Trp-Ala-Trp-D-Phe-Lys-NH2, for reducing or delaying the appearance of cellular senescence.

The present invention also pertains to the novel cosmetic use of a composition comprising said peptide for reducing or delaying the appearance of signs of skin aging, and more particularly of wrinkles.

The present invention also pertains to a cosmetic treatment method pertaining to these novel uses, comprising the steps of topical application of the composition at least once per day for a period of at least 2 days.

The skin is an enveloping organ composed of several layers (dermis, dermo-epidermal junction, epidermis). The dermis is the support tissue for the skin and is composed of water, elastin fibres and collagen fibres. This latter represents approximately 70% of the dermal fibres and is synthesized by the fibroblasts.

The synthesis of collagen, its degradation and its recycling are essential steps in maintaining its level of expression in the extracellular matrix of the skin. All of these steps are highly regulated, especially recycling. This latter step is carried out by a cytoplasmic enzyme: prolidase. Prolidase is an enzyme which degrades the imidodi- and tri-peptides containing proline or hydroxyproline in the C-terminal position and principally deriving from collagen (Surazynski et al. Amino Acids (2008) 35:731-738). Thus, because of the action of the prolidase, the reservoir of proline and hydroxyproline in the cell is renewed in order to enable fresh collagen to be synthesized. In fact, collagen is a protein composed of 23% proline and hydroxyproline, and the availability of the base elements, namely proline and hydroxyproline, is vital for the neosynthesis of collagen (Barbul A., J. Nutr. 138: 2021S-2024S, 2008). 90% of the proline used to synthesis collagen derives from the action of prolidase (Son et al., Biol. Pharm. Bull. 30(8) 1395-1399 (2007)).

In common with all of the other organs, the skin is subjected to a complex physiological process of aging. Intrinsic or chronological aging is the consequence of a genetically programmed senescence and of biochemical alterations due to endogenous factors. In the skin, this is characterized by a slow-down in the regeneration of cells and extracellular matrices, resulting in dermal and epidermal atrophy, dryness, a reduction in elasticity and firmness of the skin, and the appearance of fine lines and wrinkles. Extrinsic aging, on the other hand, is due to environmental attack such as pollution, the sun (UV radiation), diseases, lifestyle, etc. This is superimposed on intrinsic aging at zones which are chronically exposed to these attacks; this is then known as photo-aging.

Thus, between 20 and 80 years of age, the number of fibroblasts will reduce by half. In addition, when fibroblasts age, the level of collagen synthesis as well as the activity of the prolidase reduces, demonstrating the implication of this enzyme in senescence and the advantage of finding a molecular target to combat the senescence of fibroblasts (Palka et al. Tokai J Exp Clin Med., Vol. 21, No. 4-6, pp. 207-213, 1996).

Research has been able to identify the active agents which are capable of increasing the synthesis of collagen and of combatting skin aging. However, it has become necessary to identify novel compounds which are capable of effectively targeting the synthesis of collagen in the cell and of delaying cellular senescence.

The synthetic peptide with sequence His-D-Trp-Ala-Trp-D-Phe-Lys-NH2, which has the international nomenclature name INCI of hexapeptide-2, is already known for its bleaching, concealing and skin-lightening activity (Sawyer T K et al. Discovery and structure-activity relationships of novel alpha-melanocyte-stimulating hormone inhibitors. Pept Res. 1989 January-February; 2(1):140-6).

However, its effect on skin aging has not been described. On the contrary, the patent application EP 2 666 780 discloses that in concentrations of 1 μM, 10 μM and 100 μM, hexapeptide-2 has no effect on the secretion of collagen by fibroblasts cultured in vitro, while the same peptide chemically substituted with a biotin group increases the secretion of collagen at the same concentrations.

Nevertheless, biotinylated hexapeptide-2 has not had any effect on the activation of prolidase and the expression of collagen.

In contrast, during their research, the inventors have demonstrated that the synthetic peptide with sequence His-D-Trp-Ala-Trp-D-Phe-Lys-NH2, when used in lower concentrations, in the range 0.1 μM to 1 μM:
increases the expression and activity of prolidase,
increases the expression of type I and III collagens,
increases the expression of collagen I in fibroblasts which have been made senescent,
reduces or delays the expression of senescence markers in fibroblasts,
reduces the appearance of wrinkles.

They have thus demonstrated that this peptide is suitable for a cosmetic use aimed at reducing or delaying the appearance of cellular senescence and the appearance of signs of skin aging, and more particularly of wrinkles.

During the course of the present description, the synthetic peptide with sequence His-D-Trp-Ala-Trp-D-Phe-Lys-NH2 will be indiscriminately termed "the synthetic peptide" or "the peptide in accordance with the invention" or "hexapeptide-2".

Thus, the principal objective of the invention is the cosmetic use of a composition comprising, as the active agent, between 0.1 and 1 μM of a synthetic peptide with sequence His-D-Trp-Ala-Trp-D-Phe-Lys-NH2 (SEQ ID NO: 1) or one of its salts in a physiologically acceptable medium, for reducing or delaying the appearance of cellular senescence and signs of skin aging, the composition being applied topically, at least once per day, for a period of at least 2 days.

The term "skin" means the assembly of enveloping tissues constituting the skin, the mucous membranes and the hair and nails.

The expression "reduce or delay the appearance of cellular senescence" means that the peptide in accordance with the invention reduces the expression of senescence markers in human fibroblasts the senescence of which has been induced by extinction of the gene FOXO3a or for which replicative senescence has been induced by a large number of culture passes or in fact delays the appearance of these phenomena.

The term "physiologically acceptable" means solvents or media which are suitable for contact with the skin or human hair and nails without running the risk of toxicity, intolerance, instability, an allergic response and other secondary effects.

The diluted peptide in accordance with the invention is then sterilized by sterile filtration.

The term "signs of skin aging" means any modifications to the external appearance of the skin and the hair and nails due to aging such as, for example, thinning of the skin, sagging, loss of moisture, skin atony, deep wrinkles and fine lines, loss of firmness and tone, dermal atrophy or any other internal degradation of the skin, with the exception of pigmentary anomalies of the skin of the age spot or lentigo type or any other irregularity in the complexion.

Preferably, the expression "reduce the signs of skin aging" means that the peptide in accordance with the invention reduces the number, the total surface area, the total length and the total depth of wrinkles.

Advantageously, the compositions in accordance with the invention are in a form which is suitable for topical application.

The term "topical application" means that the composition comprising the peptide in accordance with the invention is applied to or spread onto the surface of the skin or a mucous membrane.

Advantageously, the composition comprising the peptide in accordance with the invention as an active agent will be applied topically at a frequency of at least once per day.

In another embodiment, the composition will be applied at a frequency of two times per day.

Advantageously, the composition comprising the peptide in accordance with the invention as an active agent will be applied topically for a period of at least 2 days.

In another embodiment, the composition will be applied for a period of at least 6 weeks.

In another embodiment, the composition will be applied for a period of at least 3 months.

The peptide in accordance with the invention is a synthetic hexapeptide with sequence His-D-Trp-Ala-Trp-D-Phe-Lys-NH2. Preferably, the peptide is in the form of a trifluoroacetate salt.

The peptide in accordance with the invention is advantageously dissolved in one or more physiologically acceptable solvents such as water, glycerol, ethanol, propanediol, butylene glycol, dipropylene glycol, ethoxylated or propoxylated diglycols, cyclic polyols or any mixture of these solvents.

Advantageously, the peptide in accordance with the invention is in solution in water.

After this dilution step, the peptide in accordance with the invention may be encapsulated or included in a cosmetic vector such as liposomes or any other microcapsule used in the field of cosmetics or adsorbed onto powdered organic polymers, mineral supports such as talcs and bentonites, and more generally dissolved in or fixed onto any physiologically acceptable vector.

The composition which may be used in accordance with the invention may be applied using any appropriate manner, in particular orally or topically (externally), and the formulations for the compositions will be adapted by the person skilled in the art.

Preferably, the compositions in accordance with the invention are in a form which is suitable for topical application. These compositions must therefore contain a physiologically acceptable medium, i.e. a medium which is compatible with the skin and the hair and nails, without any risk of discomfort during application, and encompasses all cosmetic forms.

These compositions may in particular be in the form of an aqueous, hydro-alcoholic or oily solution, an oil-in-water, water-in-oil or multiple emulsion, an aqueous or anhydrous gel, or a colloid. These compositions may also be in the form of creams, suspensions, or indeed powders, which are suitable for application to the skin, the mucous membranes, the lips and/or the hair and nails. These compositions may be fluid to a greater or lesser extent and have the appearance of a cream, a lotion, milk, a serum, a pomade, a cream, a paste or a foam. They may also be in the solid form, such as a stick, or be applied to the skin in the form of an aerosol. They may be used as a care product and/or as a product for making up the skin.

Furthermore, all of these compositions include any additive which is in routine use envisaged in the field of application as well as the adjuvants necessary for their formulations, such as co-solvents (ethanol, glycerol, benzyl alcohol, moisturiser, etc), thickening agents, diluents, emulsifiers, antioxidants, colorants, sunscreens, pigments, fillers, preservatives, fragrances, odour absorbers, essential oils, oligo-elements, essential fatty acids, surfactants, film-forming polymers, chemical or mineral filters, moisturisers or thermal waters, etc. Examples which may be cited are hydrosoluble polymers of the natural polymer type such as polysaccharides, or polypeptides, cellulose derivatives of the methylcellulose or hydroxypropylcellulose type, or in fact synthetic polymers, polaxamers, carbomers, siloxanes, PVA or PVP, and in particular polymers sold by the firm Ashland.

In each case, the person skilled in the art will take care to ensure that the adjuvants as well as their proportions are selected in a manner such that they do not have a deleterious effect on the advantageous properties which are desired for the composition of the invention. These adjuvants may, for example, be present in concentrations of 0.01% to 20% of the total weight of the composition. When the composition in accordance with the invention is an emulsion, the fatty phase may represent 5% to 80% by weight and preferably 5% to 50% by weight with respect to the total composition weight. The emulsifiers and co-emulsifiers used in the composition will be selected from those conventionally used in the field under consideration. As an example, they may be used in a proportion of 0.3% to 30% by weight with respect to the total composition weight.

Clearly, the peptide in accordance with the invention used as the active agent may be used alone or in fact in association with other active agents.

Advantageously, the compositions for use in accordance with the invention will also contain at least one other active agent intended to reinforce the action of the active agent in accordance with the invention, in the field of the prevention and improvement of signs of skin aging or indeed another active agent for expanding the range of properties of the composition under consideration.

The following classes of ingredients may be cited in a non-limiting manner: regenerative agents, anti-aging agents, anti-wrinkle agents, soothing agents, radical scavengers, anti-glycation agents, moisturisers, antibacterial agents, antifungal agents, keratolytic agents, muscle relaxants, desquamating agents, firming agents, agents stimulating the synthesis of dermal macromolecules or energy metabolism or microcirculation or nail growth or hair growth, agents modulating differentiation or pigmentation of the epidermis, agents inhibiting metallo-proteinases, or in fact sunscreens or filters.

In a more particular embodiment, in addition to the peptide in accordance with the invention, the composition in accordance with the invention will comprise:
- at least one compound which activates cytochrome c, and/or
- at least one moisturising compound, such as a compound which activates aquaporin, and/or
- at least one compound which activates sirtuins, and/or
- at least one compound which increases cellular adhesion, and/or
- at least one compound which increases the production of matrix proteins such as collagen, fibronectin, laminin, glycosaminoglycans, and/or
- at least one compound which modulates proteasome activity, and/or
- at least one compound which modulates the circadian rhythm, and/or
- at least one compound which modulates HSP proteins, and/or
- at least one compound which increases cellular energy, and/or
- at least one compound which modulates skin pigmentation, and/or
- at least one compound which activates coenzyme Q10, and/or
- at least one compound which improves the barrier function, such as a compound activating transglutaminase or HMG-CoA reductase, and/or
- at least one compound protecting mitochondria.

Said aforementioned compounds may be of natural origin, such as plant peptide moisturisers, or in fact of synthetic origin, such as peptides.

Independently of their functions, the other active agents associated with the active agent in accordance with the invention in the composition may have a very wide variety of chemical structures. Non-limiting examples which may be cited are peptides, vitamin C and its derivatives, vitamins from the B group, DHEA (dihydroepiandrosterone), phytosterols, salicylic acid and its derivatives, retinoids, flavonoids, amino sugars, azoles, metallic salts, peptide derivatives of plant origin or even polymers.

Advantageously, the peptide in accordance with the invention is present in the composition in a concentration in the range 0.1 to 1 µM, preferably in a concentration in the range 0.5 to 1 µM and yet more preferably in a concentration of strictly less than 1 µM.

Without wishing to be bound to any scientific theory, this range of concentrations represents the quantity necessary for the peptide in accordance with the invention as an active agent to obtain the desired molecular effect, defined as the optimized increase in the activity of prolidase and the synthesis of collagen.

Advantageously, this range of concentration can be used to obtain the maximum increase in the synthesis of type I and III collagens.

The invention also pertains to a cosmetic treatment method for reducing or delaying the appearance of cellular senescence and signs of skin aging, comprising topical application, at least once per day for a period of at least 2 days, of a composition comprising, as the active agent, between 0.1 and 1 µM of a synthetic peptide with sequence His-D-Trp-Ala-Trp-D-Phe-Lys-NH2 in a physiological suitable medium.

The invention and its resulting advantages will be better understood from the following non-limiting embodiment made with reference to the accompanying figures in which:

FIG. 1 represents a study of the expression of miRNA-29a 3p in human fibroblasts from donors of different ages;

FIG. 2 represents the evaluation of the effect of hexapeptide-2 on the expression of collagen I in human fibroblasts made senescent by transfection with the siRNA FOXO3a;

FIG. 3 represents the evaluation of the effect of hexapeptide-2 on the activity of β-galactosidase in human fibroblasts made senescent by replicative senescence (long-term treatment);

FIG. 4 represents the evaluation of the effect of hexapeptide-2 on the activity of β-galactosidase in human fibroblasts which are senescent by replicative senescence, in the presence of hexapeptide-2 (short-term treatment);

FIG. 5 represents the evaluation of the effect of hexapeptide-2 on the activity of prolidase in human fibroblasts made senescent by replicative senescence (long-term treatment);

FIG. 6 represents the evaluation of the effect of hexapeptide-2 on the expression of miRNA-29a 3p in human fibroblasts made senescent by replicative senescence (long-term treatment);

FIG. 7 represents the effect of 1% hexapeptide-2 on the total surface area of wrinkles, evaluated by clinical study.

FIG. 8 represents the effect of 1% hexapeptide-2 on the total length of wrinkles, evaluated by clinical study.

FIG. 9 represents the effect of 1% hexapeptide-2 on the total depth of wrinkles, evaluated by clinical study.

In the description and examples, unless specified otherwise, it should be understood that when a range it given it includes the upper and lower limits of said range.

EXAMPLE 1

Study of the Expression of Prolidase in Human Fibroblasts, in the Presence of Hexapeptide-2

The aim of this study was to determine the influence of hexapeptide-2 on the expression of prolidase in human fibroblasts.

Protocol: Cultured human fibroblasts were treated with hexapeptide-2 in a final concentration of 0.5 and 1 µM after dilution in a culture medium, for 24 hours (2 applications per day). The cells were then washed, fixed with cold methanol for 4 minutes at 4° C. The cells were incubated in the presence of a mouse monoclonal antibody specific for prolidase (LifeSpan BioSciences, Ref. LS-C115644), then of an anti-mouse secondary antibody coupled to a fluorochrome (Invitrogen, Ref. A21202). The cells were then examined under an epifluorescence microscope (Zeiss Axiovert 200M microscope). Quantification of the fluorescence was carried out from the photographs obtained.

Results: The microscope observations shown in Table 1 exhibited a significantly more intense cytoplasmic fluorescence in cells treated with hexapeptide-2 (using the Student t-test).

TABLE 1

|  | Untreated | 0.5 µM hexapeptide-2 | 1 µM hexapeptide-2 |
|---|---|---|---|
| Expression of prolidase (intensity/area of cells (%)) | 100 | 118 | 128 |

Conclusion: Hexapeptide-2 stimulates the expression of prolidase in human fibroblasts.

EXAMPLE 2

Study of the Activity of Prolidase in Human Fibroblasts, in the Presence of Hexapeptide-2

The aim of this study was to determine the influence of hexapeptide-2 on the activity of prolidase in human fibroblasts.

Protocol: Cultured human fibroblasts were treated with hexapeptide-2 in a concentration of 0.5 and 1 µM after dilution in a culture medium, for 24 hours (2 applications per day). At the same time, fibroblasts were treated with an activator and an inhibitor of prolidase: retinoic acid (Sigma, Ref. R2625) and Cpz-Pro (Bachem, Ref. 4001343). Next, the cells were detached from the dish with the aid of a 150 mM NaCl solution. After having recovered the cellular pellet and activating the prolidase with a solution containing 2 mM $MnCl_2$ for 2 hours at 37° C., the prolidase substrate was added: 47 mM of Glycine-Proline (Sigma, Ref. G3002) for 1 hour at 37° C. Next, the amount of proline contained in each sample was determined at a wavelength of 515 nm using Chinard's reagent. At the same time, a proline concentration range was produced in order to establish a calibration curve. The amount of protein was determined using the BCA protein assay kit (Thermo Scientific, Ref. 23225), which enabled the ratio of proline to the number of proteins in each sample to be recorded.

Result: The treatment with hexapeptide-2 enabled the activity of prolidase (using the Student t-test) to be significantly increased. The results are presented in Table 2 below.

TABLE 2

|  | Untreated | 0.5 µM hexapeptide-2 | 1 µM hexapeptide-2 | 1 µM retinoic acid | 10 mM Cpz-Pro |
|---|---|---|---|---|---|
| Activity of prolidase (%) | 100 | 122 | 114 | 105 | 90 |

Conclusion: Hexapeptide-2 stimulates the activity of prolidase in human fibroblasts.

EXAMPLE 3

Study of the Expression of Intracellular Collagen I in Human Fibroblasts, in the Presence of Hexapeptide-2

The aim of this study was to determine the influence of hexapeptide-2 on the expression of intracellular collagen I in human fibroblasts by flow cytometry.

Protocol: Cultured human fibroblasts were treated with hexapeptide-2 in a concentration of 0.5 and 1 µM after dilution in a culture medium, for 48 hours (2 applications per day). At the same time, fibroblasts were treated with an activator for collagen I: TGF-β (R&D system, Ref. 240B). The fibroblasts were trypsinated and the cellular pellet was recovered. The cells were then fixed with cold methanol for 15 minutes at 4° C. Immunolabelling was carried out with the aid of a mouse monoclonal antibody specific for collagen I (Millipore, Ref: anti-Collagen Type I, Clone: 5D8-G9) coupled with a fluorochrome. Next, 10 000 cells were analysed by flow cytometry (Guava EasyCyte) in order to determine the amount of fluorescence in each of them.

Results: Following analysis by flow cytometry, a more intense cytoplasmic fluorescence was detected in cells treated with hexapeptide-2. The results are presented in Table 3 below.

TABLE 3

|  | Untreated | 0.5 µM hexapeptide-2 | 1 µM hexapeptide-2 | 10 ng/ml TGF-β |
|---|---|---|---|---|
| Expression of collagen I (%) | 100 | 120 | 145 | 182 |

Conclusion: Hexapeptide-2 stimulates the expression of collagen I in human fibroblasts.

EXAMPLE 4

Study of the Expression of Collagens I and III in Human Skin, in Ex Vivo Culture in the Presence of Hexapeptide-2

The aim of this study was to determine the influence of hexapeptide-2 on the expression of collagens I and III in human skin ex vivo.

Protocol: Samples of human skin were cultured at the air/liquid interface. Hexapeptide-2 was applied topically to the samples in concentrations of 0.5 and 1 µM after dilution in a culture medium, in an amount of 2 applications per day, then the samples were incubated for 48 hours at 37° C.

These skin samples were subsequently fixed with formaldehyde then included into paraffin. 4 µm sections were then produced.

Labelling of the collagens I and III was then carried out after demasking specific sites by microwave incubation then by treatment with trypsin. The immunolabelling was carried out with the aid of a rabbit polyclonal antibody specific for collagen I (Rockland, Ref. 600-401-103-0.5), a rabbit polyclonal antibody specific for collagen III (Rockland, Ref 600-401-105-0.5), then an anti-rabbit secondary antibody coupled to a fluorochrome (Invitrogen, Ref. A21206). The cells were then examined under an epifluorescence microscope (Zeiss Axiovert 200M microscope). A quantification of the fluorescence from the photographs obtained was carried out.

Results: The microscopic observations exhibited a significantly more intense fluorescence in the dermis of biopsies treated with hexapeptide-2. The results are presented in Table 4 below.

TABLE 4

|  | Untreated | 0.5 µM hexapeptide-2 | 1 µM hexapeptide-2 |
|---|---|---|---|
| Expression of Collagen I (%) | 100 | 119 | 154 |
| Expression of Collagen III (%) | 100 | 155 | 155 |

Conclusions: Hexapeptide-2 stimulates the expression of collagens I and III in human skin ex vivo.

EXAMPLE 5

Study of the Expression of miRNA-29a 3p in Human Fibroblasts Deriving from Donors of Different Ages The aim of this study was to determine the influence of hexapeptide-2 on the expression of miRNA-29a 3p in human fibroblasts from donors of different ages, by qPCR. The miRNAs play a fundamental role in the post-transcriptional regulation of their targets by inhibiting them. It has been demonstrated in the literature that the expression of miRNA-29a increases with senescence (Mancini M. et al., 2014). By using databases such as miRanda, the targets for miRNA-29a were identified as being collagen I and prolidase.

Protocol: Human fibroblasts from 3 donors of 33, 45 and 66 years of age were treated with hexapeptide-2 in a concentration of 0.5 and 1 µM in culture medium overnight (1 application).

The miRNAs were extracted with the aid of an extraction kit (Ambion, Ref. AM1561), then reverse transcribed with a specific kit (Applied Biosystem, Ref 4374966). A real time PCR was carried out in a thermocycler using a TaqMan Gene Expression Assay specific for miRNA-29a 3p (Applied Biosystems, Ref 002112) and a TaqMan Gene Expression Assays specific for RNU44 used as the control endogen (Applied Biosystems, Ref. 001094). The relative quantification if the expression of miRNA-29a 3p was carried out by the comparative Ct method.

Result: Comparing the three ages, the expression of miRNA-29a 3p increases significantly with senescence by +32% (between 33 and 45 years old) and +48% (between 45 and 66 years old) (Student t test). At each age: 33, 45 and 66 years old, the cells treated with hexapeptide-2 showed, respectively, a significant reduction of −13%, −14% and −27% in the expression of miRNA-29a 3p (using the Student t-test). The results are presented in FIG. 1.

Conclusion: The expression of miRNA-29a 3p is reduced when the cells are treated with hexapeptide-2, which means that the negative impact of its expression on targets such as collagen and prolidase can be limited.

EXAMPLE 6

Study of the Activity of β-Galactosidase in Human Fibroblasts Made Senescent by Transfection with the siRNA FOXO3a, in the Presence of Hexapeptide-2

The aim of this study was to determine the influence of hexapeptide-2 on senescent human fibroblasts. Senescence was induced by inhibition of the FOXO3a gene using interfering RNA (siRNA) from FOXO3a. FOXO3a is a Forkhead type transcription factor involved in cellular longevity. By inhibiting the expression of FOXO3a, the cells over-express β-galactosidase, which is characteristic of senescent cells.

Protocol: Cultured human fibroblasts were treated or not treated with a specific siRNA of FOXO3a (Invitrogen, Ref. HSS177176) in a final concentration of 25 nM using the technique of transfection by Lipofectamine™ RNAiMAX (Invitrogen, Ref 56531) and treated or not treated with hexapeptide-2 in a final concentration of 1 µM in culture medium, for 48 hours (2 applications per day).

The cells were rinsed and fixed in a fixing buffer (0.2% glutaraldehyde, 2% formaldehyde). The cells were then incubated at 37° C. without $CO_2$ for 24 hours, with a solution of 1 mg/mL X-Gal in 40 mM of citric acid/phosphate (pH 6), 5 mM $K_3FeCN_6$, 5 mM $K_4FeCN_6$, 150 mM NaCl and 2 mM $MgCl_2$. The cells were then examined under white light with a microscope (Nikon Eclipse E600 microscope).

Results: The senescent cells having a specific β-galactosidase activity were stained blue. The cells treated with the specific siRNA of FOXO3a exhibited an increase in β-galactosidase linked to senescence, resulting in an increase in the number of blue-stained cells. The cells transfected with the specific siRNA of FOXO3a and treated with hexapeptide-2 exhibited a visible reduction in the activity of β-galactosidase linked to senescence, resulting in a reduction in the number of blue-stained cells (results not shown).

Conclusion: Treatment with hexapeptide-2 allowed cells to be observed for which the level of senescence was lower than untreated transfected cells.

EXAMPLE 7

Study of the Expression of Collagen I in Human Fibroblasts Made Senescent by Transfection with the siRNA FOXO3a, in the Presence of Hexapeptide-2

The aim of this study was to determine the influence of hexapeptide-2 on the expression of collagen I in senescent human fibroblasts by transfection with the siRNA FOXO3a.

Protocol: Cultured human fibroblasts were treated or not treated with a specific siRNA of FOXO3a (Invitrogen, Ref. HSS177176) in a final concentration of 25 nM using the technique of transfection by Lipofectamine™ RNAiMAX (Invitrogen, Ref. 56531) and treated or not treated with hexapeptide-2 in a concentration of 0.5 or 1 µM in culture medium, for 48 hours (2 applications per day).

The fibroblasts were trypsinated and the cellular pellet was recovered. The cells were then fixed with cold methanol for 15 minutes at 4° C. Immunolabelling was carried out with the aid of a mouse monoclonal antibody specific for collagen I (Millipore, Ref. anti-Collagen Type I, Clone: 5D8-G9) coupled with a fluorochrome. Next, 10 000 cells were analysed using flow cytometry (Guava EasyCyte) in order to determine the level of fluorescence in each of them.

Results: Following the induction of senescence by transfection with the siRNA FOXO3a, a reduction in the expression of collagen I was observed in these cells. The cells which were senescent and treated with hexapeptide-2 per se exhibited a smaller reduction in the expression of collagen I. The results are presented in FIG. 2.

Conclusion: Treatment with hexapeptide-2 can be used to limit the effects of senescence such as the reduction in the expression of collagen I.

EXAMPLE 8

Study of the Activity of β-Galactosidase in Human Fibroblasts Made Senescent by Replicative Senescence, in the Presence of Hexapeptide-2 (Long-Term Treatment)

The aim of this study was to determine the influence of hexapeptide-2 on senescent human fibroblasts. In contrast to the model of senescence obtained by transfection of the siRNA FOXO3a for which senescence was induced over 48 hours, replicative senescence is a long process which necessitates approximately 3 months. The fibroblasts were regularly sub-cultured by trypsinization in order to cause them to divide, and as a consequence to make them age.

Protocol: Human fibroblasts were cultured in a specific medium and maintained under culture (for more than 27 passes) and treated or not treated with a daily application of hexapeptide-2 in a concentration of 1 µM in the culture medium, (i.e. 5 applications per week). A portion of the cells was frozen in each pass. Next, key passes were selected: passes 4, 12, 16, 20, 24 and 27. After freezing, the senescent phenotype of the fibroblasts treated or not treated with 1 µM hexapeptide-2 was evaluated by assaying the activity of β-galactosidase.

To this end, the cells were rinsed and fixed in a fixing buffer (0.2% glutaraldehyde, 2% formaldehyde). The cells were then incubated, at 37° C. without $CO_2$ for 24 hours, with a solution of 1 mg/mL X-Gal in 40 mM of citric acid/phosphate (pH 6), 5 mM $K_3FeCN_6$, 5 mM $K_4FeCN_6$, 150 mM NaCl and 2 mM $MgCl_2$. The cells were then examined under white light with a microscope (Nikon Eclipse E600 microscope).

Results: During the course of the cell passes, the activity of the β-galactosidase increased, indicating that the level of senescence increased with each pass. When these cells were treated with 1 µM hexapeptide-2, we observed a general, significant reduction of −22% in the activity of beta-galactosidase compared with untreated cells (using the Student t-test). The results are shown in FIG. 3.

Conclusion: Following a long-term treatment of approximately 3 months, we observed that the degree of senescence in cells treated with hexapeptide-2 was lower than in the untreated cells. Thus, the treatment with hexapeptide-2 could slow down cell aging.

EXAMPLE 9

Study of the Activity of β-Galactosidase in Senescent Human Fibroblasts by Replicative Senescence, in the Presence of Hexapeptide-2 (Short-Term Treatment)

The aim of this study was to determine the influence of hexapeptide-2 on senescent human fibroblasts by replicative senescence.

Protocol: Human fibroblasts were cultured in a specific medium and maintained under long-term culture treatment (for more than 28 passes, i.e. approximately 3 months). A portion of the cells was frozen in each pass. Next, key passes were selected: passes 4, 12, 16, 20 and 28. After freezing, the fibroblasts were treated with 1 µM hexapeptide-2 in culture medium, for 48 hours (2 applications per day). The senescent phenotype of the fibroblasts treated or not treated with 1 µM hexapeptide-2 was evaluated by assaying the activity of the β-galactosidase.

To this end, the cells were rinsed and fixed in a fixing buffer (0.2% glutaraldehyde, 2% formaldehyde). The cells were then incubated, at 37° C. without $CO_2$ for 24 hours, with a solution of 1 mg/mL X-Gal in 40 mM of citric acid/phosphate (pH 6), 5 mM $K_3FeCN_6$, 5 mM $K_4FeCN_6$, 150 mM NaCl and 2 mM $MgCl_2$. The cells were then examined under white light with a microscope (Nikon Eclipse E600 microscope).

Results: During the course of the cell passes, the activity of β-galactosidase increased, indicating the level of senescence of each pass. When these cells, which had been made senescent, were treated with 1 µM hexapeptide-2, we observed a general significant reduction of −31% in the activity of the β-galactosidase compared with untreated cells (using the Student t-test). The results are presented in FIG. 4.

Conclusion: Following a short-term treatment of 48 hours, we observed that the cells treated with hexapeptide-2 had a lower level of senescence than the untreated cells. Thus, treatment with hexapeptide-2 could be used to slow down cellular aging.

EXAMPLE 10

Study of the Activity of Prolidase in Human Fibroblasts Made Senescent by Replicative Senescence, in the Presence of Hexapeptide-2 (Long-Term Treatment)

The aim of this study was to determine the influence of hexapeptide-2 on the activity of prolidase in senescent human fibroblasts. It has been shown in the literature that the activity of prolidase reduces with cellular aging, and this is correlated with the reduction in collagen I observed in senescent cells (Palka et al. Tokai J Exp Clin Med 1996).

Protocol: Human fibroblasts were cultured in a specific medium and maintained under long-term culture treatment (for more than 20 passes, i.e. approximately 3 months), treated or not treated with the aid of a daily application of hexapeptide-2 in a concentration of 1 µM in culture medium, (5 applications per week). A portion of the cells was frozen for each pass. Next, two passes were selected: passes 12 and 20. After freezing, the activity of prolidase was observed for these conditions.

To this end, the cells were detached from their support with a solution of 150 mM NaCl. After recovering the cellular pellet and activating the prolidase with a solution containing 2 mM of $MnCl_2$ for 2 hours at 37° C., the substrate for the prolidase was added: 47 mM of Glycine-Proline (Sigma, Ref. G3002), for 1 hour at 37° C. Next, the proline content contained in each sample was determined at a wavelength of 515 nm using Chinard's reagent. At the same time, a concentration range for proline was produced in order to establish a calibration curve. The protein content was determined using the BCA protein assay kit (Thermo Scientific, Ref. 23225), in order to relate the proline content with the number of proteins in each sample.

Result: The comparison of the passes P12 (cells considered to be young) and P20 (cells considered to be senescent) show that the activity of the prolidase reduces by 36% (significant value using the Student t-test) during replicative senescence. Interestingly, while hexapeptide-2 had little or no effect on young cells (P12), the application of hexapeptide-2 to senescent cells (P20) showed a restoration of 20% (significant value using the Student t-test) in the activity of prolidase compared with untreated control cells in the same pass.

The results are shown in FIG. 5.

Conclusion: During senescence, the activity of prolidase reduces, along with the expression of collagen. Treatment with hexapeptide-2 could allow the activity of prolidase to be maintained, thereby resulting in collagen recycling being maintained.

EXAMPLE 11

Study of the Expression of miRNA-29a 3p in Human Fibroblasts Made Senescent by Replicative Senescence, in the Presence of Hexapeptide-2 (Long-Term Treatment)

The aim of this study was to determine the influence of hexapeptide-2 on the expression of miRNA-29a 3p in senescent human fibroblasts, by replicative senescence. The miRNAs play a fundamental role in post-transcriptional regulation of their targets by inhibiting them. It has been shown in the literature that the expression of miRNA-29a increases with senescence (Mancini M. et al., 2014). By means of databases such as miRanda, the targets for miRNA-29a were identified, including collagen I and prolidase.

Protocol: Human fibroblasts were cultured in a specific medium and maintained under a long-term culture treatment (for more than 24 passes, i.e. approximately 3 months), treated or not treated by means of a daily application of hexapeptide-2 in a concentration of 1 µM in culture medium, (5 applications per week). For each pass, a portion of the cells was frozen. Next, three passes were selected: passes 4, 12 and 24. After freezing, the expression of miRNA-29a 3p was observed for these conditions, by quantitative PCR.

The miRNAs were extracted with the aid of an extraction kit (Ambion, Ref AMI1561), then reverse transcribed with a specific kit (Applied Biosystems, Ref 4374966). A real-time PCR was carried out in a thermocycler with the aid of a TaqMan Gene Expression Assay specific for miRNA-29a 3p (Applied Biosystems, 002112) and a TaqMan Gene Expression Assay specific for RNU44 used as an endogenic control (Applied Biosystems, 001094). The relative quantification of the expression of miRNA-29a 3p was carried out using the comparative Ct method.

Result: Following a comparison of the three passes P4, P12 and P20, we could observe that the expression of miRNA-29a 3p increased significantly by +25% (between P4 and P12) and +52% (between P4 and P24) (Student t test) with senescence. At pass 4, no effect of hexapeptide-2 was observed on the expression of miRNA-29a 3p. In contrast, at passes 12 and 24, the cells treated with hexapeptide-2 respectively exhibited a significant reduction of −16% and of −7% in the expression of miRNA-29a 3p (using the Student t-test). The results are shown in FIG. 6.

Conclusion: The cells treated with 1 µM hexapeptide-2 appeared to maintain a certain level of expression of miRNA-29a 3p despite senescence, thus allowing the negative impact of its expression on targets such as collagen and prolidase to be limited.

EXAMPLE 12

Preparation of an Anti-Aging Cosmetic Composition for the Face

| Commercial names | INCI names | % by weight |
|---|---|---|
| PHASE A | | |
| Demineralized water | Aqua | 76.80 |
| Na4 EDTA | Tetrasodium EDTA | 0.05 |
| Lubrasil ™ II DM | Glycerin & Glyceryl Acrylate/Acrylic Acid Copolymer & Laureth-23 & Dimethicone | 3.00 |
| Liquapar MEP | Phenoxyethanol & Methylparaben & Ethylparaben & Propylparaben | 1.00 |
| PHASE B | | |
| UltraThix ® P-100 | Acrylic Acid/VP Crosspolymer | 0.60 |
| PHASE C | | |
| NaOH Pearls | Sodium Hydroxide | 0.02 |
| Demineralized water | Aqua | 0.50 |
| PHASE D | | |
| Belsil SDM 6022 | Stearoxy Dimethicone & Dimethicone | 2.00 |
| Simulsol 165 | PEG-100 Stearate & Glyceryl Stearate | 2.00 |
| Refined Shea Butter | Butyrospermum Parkii (Shea) Butter | 2.00 |
| Ceraphyl ® 28 | Cetyl Lactate | 1.50 |
| Ceraphyl ® 791 | Isocetyl Stearoyl Stearate | 2.00 |
| Ceraphyl ® ODS | Octyldodecyl Stearate | 3.00 |
| Ceraphyl ® 368 | Ethylhexyl Palmitate | 4.00 |
| PHASE E | | |
| NaOH Pearls | Sodium Hydroxide | 0.03 |
| Demineralized water | Aqua | 0.50 |
| PHASE F | | |
| Hexapeptide-2 | | 1.00 |
| | | 100.00 |

Under the conditions for the preparation of this formula, the 1% hexapeptide-2 corresponds to a concentration of 1 µM.

The cosmetic composition for the face termed the "placebo" was produced in exactly the same manner, with the exception that the hexapeptide-2 was replaced with purified water.

EXAMPLE 13

Study of the Effect of 1% Hexapeptide-2 on the Appearance of Wrinkles (Clinical Study)

Aim: Clinical study regarding the appearance of wrinkles after topical treatment with a cosmetic composition comprising 1% hexapeptide-2, against placebo.

Protocol:
Number of participants: 35 (aged 35 to 65 years of age).
Study: double blind study against placebo.
Products tested: hexapeptide-2, 1% formulation (i.e. a final concentration of 1 µM) in a cosmetic composition as described in Example 12 versus the placebo composition. Under the conditions of:
Number of applications: 2 applications per day, morning and evening, in a dose of 2 mg/cm$^2$.
Duration of test: 6 weeks.
Control visits: Day 0 (D0), and Day 42 (D42).
Measurements: analysis of silicone replicas made of the crow's feet using Visioline®
VL650 software
Statistical analyses: either the "t" Student test or Wilcoxon test was used, depending on the normality of the distribution of the data.

Results: After application of hexapeptide-2 in a 1% formula in the composition in accordance with Example 12, the analysis of silicone replicas exhibited a statistically significant reduction on D42 in the number, total surface area, total length, total depth and maximum depth of the wrinkles compared with the placebo. The results are presented in FIGS. 7, 8 and 9 and in Table 5 below.

TABLE 5

| | Treatment | Time | Mean | Sem | p | % change | % improvement in participants |
|---|---|---|---|---|---|---|---|
| Number of wrinkles | Placebo | D42-D0 | −7.83 | 14.97 | 0.0206* | −12.47% | 57% |
| | 1% hexapeptide-2 | D42-D0 | −53.14 | 17.36 | | | |
| Total surface area of wrinkles (mm²) | Placebo | D42-D0 | −1.29 | 1.64 | 0.0093** | −27.59% | 63% |
| | 1% hexapeptide-2 | D42-D0 | −6.85 | 1.33 | | | |
| Total length (mm) | Placebo | D42-D0 | −10.17 | 11.84 | 0.0281* | −17.48% | 66% |
| | 1% hexapeptide-2 | D42-D0 | −43.99 | 10.62 | | | |
| Total depth (μm) | Placebo | D42-D0 | −364.44 | 716.25 | 0.0088** | −15.75% | 60% |
| | 1% hexapeptide-2 | D42-D0 | −3030.34 | 850.01 | | | |
| Maximum depth (μm) | Placebo | D42-D0 | 8.68 | 10.81 | 0.0021** | −23.13% | 63% |
| | 1% hexapeptide-2 | D42-D0 | −43.06 | 10.29 | | | |

*significant;
**very significant, with the Student test or the Wilcoxon test (test selected as a function of the normality of the distribution of the data);
mean n = 35 +/− sem.

Conclusions: The topical application of 1% hexapeptide-2 (i.e. in a concentration of 1 μM) over 42 days causes a statistically significant reduction in the appearance of wrinkles.

Applicants incorporate by reference the material contained in the accompanying computer readable Sequence Listing entitled "BV15-176PCT Sequence Listing ST25", which was created on Oct. 4, 2017, and is 731 bytes in size.

The invention claimed is:

1. A method for increasing the activity of prolidase and the synthesis of collagen in skin, the method comprising topically applying a composition comprising, as the only active agent, between 0.1 and 1 μM of a synthetic peptide with sequence His-D-Trp-Ala-Trp-D-Phe-Lys-NH2 (SEQ ID NO: 1) or one of its salts in a physiologically acceptable medium, wherein the composition is applied topically, at least once per day, for a period of at least 2 days.

2. The method of claim 1, wherein the composition comprises between 0.5 and 1 μM of said synthetic peptide.

3. The method of claim 1, wherein the composition comprises less than 1 μM of said synthetic peptide.

4. The method of claim 1, wherein the composition is applied 2 times per day.

5. The method of claim 1, wherein the composition is applied over a period of at least 6 weeks.

6. The method of claim 1, wherein the composition is applied over a period of at least 3 months.

7. A cosmetic treatment method for reducing or delaying the appearance of cellular senescence and the signs of skin aging, the method comprising the topical application, at least once per day over a period of at least 2 days, of a composition comprising, as the only active agent, between 0.1 and 1 μM of a synthetic peptide with the sequence His-D-Trp-Ala-Trp-D-Phe-Lys-NH2 (SEQ ID NO: 1) in a physiologically acceptable medium, where the composition increases the activity of prolidase and the synthesis of collagen.

8. The method of claim 1, wherein the method reduces or delays the appearance of cellular senescence and signs of skin aging selected from thinning of the skin, sagging, toss of moisture, skin atony, deep wrinkles and fine lines, loss of firmness and tone, dermal atrophy with the exception of pigmentary anomalies of the skin.

9. The method of claim 8, wherein the signs of skin aging are wrinkles.

\* \* \* \* \*

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Configuration D
<220> FEATURE:
<221> NAME/KEY: MISC_FEATURE
<222> LOCATION: (5)..(5)
<223> OTHER INFORMATION: Configuration D
<220> FEATURE:
<221> NAME/KEY: MOD_RES
<222> LOCATION: (6)..(6)
<223> OTHER INFORMATION: AMIDATION

<400> SEQUENCE: 1

His Trp Ala Trp Phe Lys
1               5
```